United States Patent [19]

Levy

[11] Patent Number: 5,114,418
[45] Date of Patent: May 19, 1992

[54] HIGHLY ABSORBENT, LEAK-PROOF AND BREATHABLE DIAPER

[76] Inventor: Harry Levy, 219-04 Stewart Rd., Hollis Hills, N.Y. 11427

[21] Appl. No.: 625,148

[22] Filed: Dec. 10, 1990

[51] Int. Cl.⁵ ............................................. A61F 13/15
[52] U.S. Cl. ................................... 604/365; 604/371; 604/372; 604/370
[58] Field of Search ............... 604/365, 367, 370, 366, 604/371, 372, 385.1

[56] References Cited

U.S. PATENT DOCUMENTS

| | | | |
|---|---|---|---|
| 3,367,333 | 2/1968 | Scheier | 604/378 X |
| 3,654,060 | 4/1972 | Goldman | 604/370 X |
| 3,719,189 | 3/1973 | Sherman | 604/370 |
| 4,704,117 | 11/1987 | Mitchell | 604/391 |
| 4,718,902 | 1/1988 | Bonito | 604/396 |
| 4,943,286 | 7/1990 | Armstead | 604/365 X |
| 4,961,982 | 10/1990 | Taylor | 604/369 X |

*Primary Examiner*—Randall L. Green
*Assistant Examiner*—D. Willse
*Attorney, Agent, or Firm*—Charles I. Brodsky

[57] ABSTRACT

The highly absorbent, leak-proof and breathable diaper of the invention is a 3-layer fabric incorporating a first layer of terry cloth, a second layer of polyurethane film, and a third layer of woven, or knit, fabric. Both the first and second layers, and the second and third layers, are laminated together with a urethane adhesive. The first layer then serves as a fluid absorbing portion for the diaper, while the second and third layers form a leakage-preventing portion for it.

4 Claims, 1 Drawing Sheet

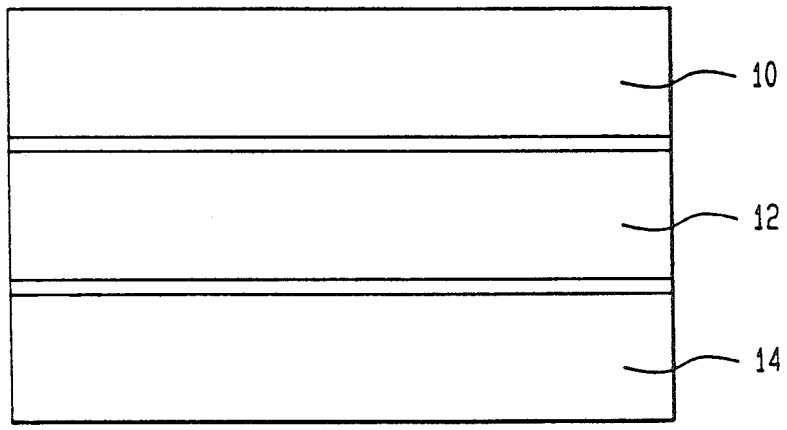

HIGHLY ABSORBENT, LEAK-PROOF AND BREATHABLE DIAPER

FIELD OF THE INVENTION

This invention relates to durable and reusable diapers and, more particularly, to a diaper construction which is highly absorbent, leak-proof and breathable.

BACKGROUND OF THE INVENTION

As is well known and understood, we presently live in an age where environmental issues are of prominent concern, both to individuals, industry, and Government. One need only pick-up a newspaper or magazine, or watch television, or listen to the radio, to hear of new fears and concerns, almost daily. One of the major areas of consideration is that of the "disposability" of products employed in the health industry. One specific matter undergoing evaluation is the "disposabiilty" of diapers—whether used for infants or incontinent adults—especially with decreasing numbers of landfills available.

For such reason, increasing attention has been given to the idea of developing a durable and reusable diaper, even though the convenience of the "disposable" diaper has been well established over the past 10-20 years. More and more attention has been given to the concept of developing a highly absorbent, leak-proof and breathable diaper, but one which can be reused and which can withstand hundreds of washings and dryings.

SUMMARY OF THE INVENTION

As will become clear hereinafter, the diaper of the invention is a 3-layer fabric, incorporating a first layer of terry cloth, a second layer of polyurethane film, and a third layer of woven or knit fabric. Both the first and second layers, and the second and third layers, will be seen to be laminated together, with a urethane adhesive. The first layer then serves as the fluid absorbing portion for the diaper, while the second and third layers form a leakage-preventing portion for it, and in manner to enable the diaper to be reusable, and durable, throughout its extended lifetime.

BRIEF DESCRIPTION OF THE DRAWING

These and other features of the invention will be more clearly understood from a consideration of the following description, taken in conjunction with the sole figure of the drawing indicative of the construction of the diaper which is, at the same time, reusable, highly absorbent, leak-proof, breathable and durable.

DETAILED DESCRIPTION OF THE DRAWING

In accordance with the present invention, a 3-layer fabric is described which offers the features of being reusable, highly absorbing, leak-proof, breathable, and durable, even after hundreds of commercial washing cycles and dryings. The first layer (shown by the reference numeral 10) is selected of a highly absorbent terry cloth made of a polyester/cotton blend. In a preferred embodiment, a terry cloth of weight 2.0 oz/yd$^2$ was employed, although different weights and/or different fiber contents may be employed, all dependent upon the degree of absorbency needed, the "weight" requirements of the diaper, and upon its ultimate end use, as whether required for infants of differing weights or adults of different degrees of incontinence. It will be appreciated, by those skilled in the art, that it is this terry cloth layer 10 which will contact the body of the wearer.

Also shown in the drawing is the leakage-preventing portion of the diaper, composed of the second and third layers 12, 14—it being understood that the first layer 10 serves as a fluid-absorbing portion as to urine, fluids, or other moistures and wastes. In accordance with the invention, the second layer 12 is a polyurethane film, preferably of 0.002 inch thickness, for serving as part of the leakage-preventing portion of the diaper fabric, along with a bottom layer 14 to be exposed to the ambient conditions. This third, or bottom, layer 14, according to the invention, may be a fabric in the nature of a 2.2 oz/yd$^2$ brushed polyester knit, a brushed nylon knit, a brushed cotton knit, a 70 denier polyester knit or any other suitable denier polyester, a nylon or cotton knit, or a blend of any of the foregoing, or a further terry cloth, comparable to that comprising the first layer fabric 10. As with that layer 10, a variety of weights and/or fibers may be selected, depending upon the degree of absorbency needed, the "weights" of the infant wearers, and generally upon the end-use needs of the situation.

In accordance with a preferred embodiment of the invention, the first and second layers 10-12, and the second and third layers 12-14, are each laminated together with a urethane adhesive. For highly satisfactory results, a non-flammable solvent-based urethane adhesive was employed, and of a two-component polyurethane system. In fabrication, the adhesive was applied between the layers 10-12, and between the layers 12-14 using a cross-hatch, line-gravure, or dot-roller, so as to give a satisfactory level of bond strength and to insure that the resulting laminations remain intact after machine washings. To construct the lamination, the adhesive was cured using heat for reactivation, and the laminate was allowed to sit for 24 hours to complete the curing process. In a preferred fabrication, the layers 12-14 were first laminated together, and after the lamination was allowed to sit this 24 hours, it was then laminated to the layer 10.

In a preferred embodiment of the invention, the polyurethane film was selected of a high water vapor permeability, of the order of 360 g/m$^2$/24 hrs., and of a thickness of 0.051 mm. With a specific gravity of 1.1-12, a hydrostatic resistance of 62 psi, and a tensile strength of 4-10 psi, the film exhibited a very high resistance to abrasion and tearing. When composed of a polyether urethane, the layer 12 also exhibited an elongation of over 250%, and had a high chemical resistance to alkali and detergent solutions.

In tests made of the diaper fabric, over hundreds of washings were made with a commercial machine incorporating various wash, rinse, bleach, and souring cycles, although not necessarily in that order, and then subjected to dryings at temperatures of 160° F., before starting a "wash" cycle anew. With additions of 16 oz alkali/ 8 oz detergent solutions, 1% sodium hypochlorite bleaches and souring to ph 5.5, no delamination, or "bubbling" was observable between any of the layers even after 200 washings and subsequent dryings. In such testings, only non-ionic detergents were employed, and no softeners were utilized as such solutions tend to reduce the absorbency of the fabrics employed.

With the composition of the diaper fabric as set forth above, analysis has also shown that after this continued washing and drying, there did not appear any uneven shrinkage between the terry cloth fluid absorbing portion and the polyurethane-woven, or knit, fabric leakage-preventing portion. This adds to the comfortableness of the diaper for the user, and along with the fabrics employed, gave the diaper a highly desirable "breathable" characteristic.

In the preferred embodiment of the invention, a completed construction was finalized with the lamination of the layers 10 and 12, and with the lamination of the layers 12 and 14, using an adhesive mixture formed of the composition:

1) polyurethane adhesive of viscosity 5,000 cps±2,000 cps —16.67% by weight; and
2) polyurethane adhesive of viscosity 27,000 cps±2,500 cps —83.33% by weight.

Such polyurethane adhesives are generally available and manufactured by Soluol Chemical Co., Inc., of West Warwick, R.I., under the Tradenames Solubond 1101 and Solubond 1173, respectively.

While there have been described what are considered to be preferred embodiments of the present invention, it will be readily apparent to those skilled in the art that modifications can be made without departing from the scope of the teachings herein. For at least such reason, therefore, resort should be had to the claims appended hereto for a true understanding of the scope of the invention.

I claim:

1. A breathable, durable and reusable diaper, comprising:

a first layer of terry cloth for providing a high absorbency characteristic to urine, fluids, moisture and body wastes;

a second layer of polyurethane film for providing a high leakage preventing characteristic to urine, fluids, moisture and body wastes absorbed by said first layer;

a first urethane adhesive joined between said first and second layers for laminating together said first and second layers;

a third layer of one of woven or knit fabric, also for providing a high leakage preventing characteristic to urine, fluids, moisture and body wastes absorbed by said first layer;

a second urethane adhesive joined between said second and third layers for laminating together said second and third layers; and with said first layer, when said diaper is worn, structured to be in contact with the body of the wearer.

2. The diaper of claim 1 wherein said first and second urethane adhesives incorporate a non-flammable solvent-based urethane adhesive.

3. The diaper of claim 1 wherein said terry cloth is composed of a polyester/cotton blend of weight substantially 2.0 oz/yd$^2$.

4. The diaper of claim 1 wherein said first and second urethane adhesives include adhesive mixtures composed of the formulation by weight of:

polyurethane adhesive of viscosity 5,000 cps±2,000 cps —16.67%; and
polyurethane adhesive of viscosity 27,000 cps±2,500 cps —83.33%.

* * * * *